(12) United States Patent
Shadduck et al.

(10) Patent No.: US 8,419,723 B2
(45) Date of Patent: *Apr. 16, 2013

(54) METHODS FOR TREATMENT OF PROSTATIC TISSUE

(75) Inventors: John H. Shadduck, Tiburon, CA (US); Michael Hoey, Shoreview, MN (US)

(73) Assignee: NxThera, Inc., Maple Grove, MN (US)

( * ) Notice: Subject to any disclaimer, the term of this patent is extended or adjusted under 35 U.S.C. 154(b) by 699 days.

This patent is subject to a terminal disclaimer.

(21) Appl. No.: 12/614,238

(22) Filed: Nov. 6, 2009

(65) Prior Publication Data

US 2010/0145254 A1 Jun. 10, 2010

Related U.S. Application Data

(60) Provisional application No. 61/112,099, filed on Nov. 6, 2008.

(51) Int. Cl.
*A61B 18/04* (2006.01)

(52) U.S. Cl.
USPC .................. 606/27; 606/41; 604/517

(58) Field of Classification Search ............ 606/27; 607/104, 105, 113; 604/113
See application file for complete search history.

(56) References Cited

U.S. PATENT DOCUMENTS

| 4,672,963 A | 6/1987 | Barken |
| 4,950,267 A | 8/1990 | Ishihara et al. |
| 5,312,399 A * | 5/1994 | Hakky et al. ............ 606/15 |
| 5,330,518 A | 7/1994 | Neilson et al. |
| 5,366,490 A | 11/1994 | Edwards et al. |
| 5,370,609 A | 12/1994 | Drasler et al. |
| 5,370,675 A * | 12/1994 | Edwards et al. ............ 607/101 |
| 5,385,544 A | 1/1995 | Edwards et al. |
| 5,409,453 A | 4/1995 | Lundquist et al. |
| 5,421,819 A | 6/1995 | Edwards et al. |
| 5,435,805 A | 7/1995 | Edwards et al. |
| 5,470,308 A | 11/1995 | Edwards et al. |

(Continued)

FOREIGN PATENT DOCUMENTS

| WO | WO 92/10142 A1 | 6/1992 |
| WO | WO 01/24715 A1 | 4/2001 |
| WO | WO 2006/004482 A1 | 1/2006 |

OTHER PUBLICATIONS

HAI; Photoselective Vaporization Prostatectomy: A Palliative Treatment Option for Men with Urinary Obstruction Secondary to Prostate Cancer; PCRI Prost.Cancer Rsrch.Inst. Reprint.from PCRI Insights Nov. 2005, vol. 8(4); Dwnld from http://www.prostate-cancer.org/pcricms/node/233 on May 10, 2012; 4 pages.

(Continued)

*Primary Examiner* — Linda Dvorak
*Assistant Examiner* — Jocelyn D Ram
(74) *Attorney, Agent, or Firm* — Shay Glenn LLP

(57) ABSTRACT

A prostate therapy system is provided that may include any of a number of features. One feature of the prostate therapy system is that it can access a prostate lobe transurethrally. Another feature of the prostate therapy system is that it can deliver condensable vapor into the prostate to ablate the prostate tissue. Another feature of the prostate therapy system is that it can aspirate tissue from the prostate. Yet another feature of the prostate therapy system is that it can rotate during delivery of vapor and aspiration of tissue. Methods associated with use of the prostate therapy system are also covered.

12 Claims, 10 Drawing Sheets

U.S. PATENT DOCUMENTS

| | | | | |
|---|---|---|---|---|
| 5,470,309 | A | 11/1995 | Edwards et al. | |
| 5,484,400 | A | 1/1996 | Edwards et al. | |
| 5,531,676 | A | 7/1996 | Edwards et al. | |
| 5,542,915 | A | 8/1996 | Edwards et al. | |
| 5,542,916 | A | 8/1996 | Hirsch et al. | |
| 5,545,171 | A | 8/1996 | Sharkey et al. | |
| 5,549,644 | A | 8/1996 | Lundquist et al. | |
| 5,554,110 | A | 9/1996 | Edwards et al. | |
| 5,556,377 | A | 9/1996 | Rosen et al. | |
| 5,558,673 | A | 9/1996 | Edwards et al. | |
| 5,588,960 | A | 12/1996 | Edwards et al. | |
| 5,591,125 | A | 1/1997 | Edwards et al. | |
| 5,599,294 | A | 2/1997 | Edwards et al. | |
| 5,601,591 | A | 2/1997 | Edwards et al. | |
| 5,630,794 | A | 5/1997 | Lax et al. | |
| 5,667,488 | A | 9/1997 | Lundquist et al. | |
| 5,672,153 | A | 9/1997 | Lax et al. | |
| 5,720,718 | A | 2/1998 | Rosen et al. | |
| 5,720,719 | A | 2/1998 | Edwards et al. | |
| 5,797,903 | A | 8/1998 | Swanson et al. | |
| 5,800,486 | A * | 9/1998 | Thome et al. | 607/105 |
| 5,830,179 | A | 11/1998 | Mikus et al. | |
| 5,849,011 | A | 12/1998 | Jones et al. | |
| 5,871,481 | A | 2/1999 | Kannenberg et al. | |
| 5,873,877 | A * | 2/1999 | McGaffigan et al. | 606/41 |
| 5,944,715 | A | 8/1999 | Goble et al. | |
| 5,957,922 | A | 9/1999 | Imran | |
| 5,964,752 | A | 10/1999 | Stone | |
| 5,964,756 | A | 10/1999 | McGaffigan et al. | |
| 5,976,123 | A | 11/1999 | Baumgardner et al. | |
| 6,007,571 | A * | 12/1999 | Neilson et al. | 607/105 |
| 6,017,361 | A | 1/2000 | Mikus et al. | |
| 6,036,713 | A | 3/2000 | Kieturakis | |
| 6,077,257 | A | 6/2000 | Edwards et al. | |
| 6,113,593 | A | 9/2000 | Tu et al. | |
| 6,179,836 | B1 * | 1/2001 | Eggers et al. | 606/45 |
| 6,206,847 | B1 | 3/2001 | Edwards et al. | |
| 6,231,591 | B1 | 5/2001 | Desai | |
| 6,238,389 | B1 | 5/2001 | Paddock et al. | |
| 6,238,391 | B1 | 5/2001 | Olsen et al. | |
| 6,241,702 | B1 | 6/2001 | Lundquist et al. | |
| 6,258,087 | B1 | 7/2001 | Edwards et al. | |
| 6,287,297 | B1 | 9/2001 | Woodruff et al. | |
| 6,423,027 | B1 | 7/2002 | Gonon | |
| 6,440,127 | B2 | 8/2002 | McGovern et al. | |
| 6,517,534 | B1 | 2/2003 | McGovern et al. | |
| 6,524,270 | B1 * | 2/2003 | Bolmsjo et al. | 604/22 |
| 6,551,300 | B1 | 4/2003 | McGaffigan | |
| 6,565,561 | B1 * | 5/2003 | Goble et al. | 606/41 |
| 6,575,968 | B1 * | 6/2003 | Eggers et al. | 606/41 |
| 6,607,529 | B1 | 8/2003 | Jones et al. | |
| 6,669,694 | B2 | 12/2003 | Shadduck | |
| 6,716,252 | B2 | 4/2004 | Lazarovitz et al. | |
| 6,719,738 | B2 | 4/2004 | Mehier | |
| 6,726,696 | B1 | 4/2004 | Houser et al. | |
| 6,730,079 | B2 | 5/2004 | Lovewell | |
| 6,760,616 | B2 | 7/2004 | Hoey et al. | |
| 6,780,178 | B2 | 8/2004 | Palanker et al. | |
| 6,827,718 | B2 | 12/2004 | Hutchins et al. | |
| 6,905,475 | B2 | 6/2005 | Hauschild et al. | |
| 6,969,376 | B2 | 11/2005 | Takagi et al. | |
| 6,974,455 | B2 | 12/2005 | Garabedian et al. | |
| 7,014,652 | B2 | 3/2006 | Cioanta et al. | |
| 7,089,064 | B2 | 8/2006 | Manker et al. | |
| 7,130,697 | B2 | 10/2006 | Chornenky et al. | |
| 7,261,709 | B2 | 8/2007 | Swoyer et al. | |
| 7,261,710 | B2 | 8/2007 | Elmouelhi et al. | |
| 7,335,197 | B2 | 2/2008 | Sage et al. | |
| 7,429,262 | B2 * | 9/2008 | Woloszko et al. | 606/46 |
| 7,470,228 | B2 | 12/2008 | Connors et al. | |
| 7,674,259 | B2 * | 3/2010 | Shadduck | 606/41 |
| 8,216,217 | B2 * | 7/2012 | Sharkey et al. | 606/27 |
| 8,244,327 | B2 | 8/2012 | Fichtinger et al. | |
| 8,251,985 | B2 * | 8/2012 | Hoey et al. | 606/27 |
| 2002/0177846 | A1 * | 11/2002 | Mulier et al. | 606/27 |
| 2003/0069575 | A1 | 4/2003 | Chin et al. | |
| 2003/0130575 | A1 | 7/2003 | Desai | |
| 2004/0068306 | A1 | 4/2004 | Shadduck | |
| 2004/0230316 | A1 | 11/2004 | Cioanta et al. | |
| 2005/0096629 | A1 | 5/2005 | Gerber et al. | |
| 2005/0159676 | A1 | 7/2005 | Taylor et al. | |
| 2006/0135955 | A1 | 6/2006 | Shadduck | |
| 2006/0178670 | A1 | 8/2006 | Woloszko et al. | |
| 2006/0224154 | A1 * | 10/2006 | Shadduck et al. | 606/41 |
| 2006/0276871 | A1 | 12/2006 | Lamson et al. | |
| 2007/0032785 | A1 | 2/2007 | Diederich et al. | |
| 2007/0142846 | A1 | 6/2007 | Catanese, III et al. | |
| 2008/0021484 | A1 | 1/2008 | Catanese, III et al. | |
| 2008/0021485 | A1 | 1/2008 | Catanese, III et al. | |
| 2008/0033232 | A1 | 2/2008 | Catanese, III et al. | |
| 2008/0033458 | A1 | 2/2008 | McLean et al. | |
| 2008/0033488 | A1 | 2/2008 | Catanese, III et al. | |
| 2008/0039833 | A1 | 2/2008 | Catanese, III et al. | |
| 2008/0039872 | A1 | 2/2008 | Catanese, III et al. | |
| 2008/0039874 | A1 | 2/2008 | Catanese, III et al. | |
| 2008/0039875 | A1 | 2/2008 | Catanese, III et al. | |
| 2008/0039876 | A1 | 2/2008 | Catanese, III et al. | |
| 2008/0039893 | A1 | 2/2008 | McLean et al. | |
| 2008/0039894 | A1 | 2/2008 | Catanese, III et al. | |
| 2008/0046045 | A1 | 2/2008 | Yon et al. | |
| 2008/0132826 | A1 | 6/2008 | Shadduck et al. | |
| 2008/0208187 | A1 | 8/2008 | Bhushan et al. | |
| 2008/0249399 | A1 | 10/2008 | Appling et al. | |
| 2008/0275440 | A1 | 11/2008 | Kratoska et al. | |
| 2009/0018553 | A1 | 1/2009 | McLean et al. | |
| 2009/0054871 | A1 | 2/2009 | Sharkey et al. | |
| 2009/0149846 | A1 | 6/2009 | Hoey et al. | |
| 2009/0216220 | A1 * | 8/2009 | Hoey et al. | 606/27 |
| 2009/0227998 | A1 | 9/2009 | Aljuri et al. | |
| 2009/0277457 | A1 | 11/2009 | Hoey et al. | |
| 2010/0016757 | A1 | 1/2010 | Greenburg et al. | |
| 2010/0049031 | A1 | 2/2010 | Fruland et al. | |
| 2010/0114083 | A1 * | 5/2010 | Sharma | 606/27 |
| 2010/0145325 | A1 * | 6/2010 | Hoey et al. | 606/27 |
| 2010/0179528 | A1 * | 7/2010 | Shadduck et al. | 606/27 |
| 2010/0204688 | A1 * | 8/2010 | Hoey et al. | 606/27 |
| 2010/0286679 | A1 | 11/2010 | Hoey et al. | |
| 2010/0292767 | A1 | 11/2010 | Hoey et al. | |
| 2010/0298948 | A1 | 11/2010 | Hoey et al. | |
| 2011/0319759 | A1 | 12/2011 | Liu et al. | |

OTHER PUBLICATIONS

Hoey et al.; U.S. Appl. No. 12/614,218 entitled "Systems and Methods for Treatment of Prostatic Tissue," filed Nov. 6, 2009.

Hoey et al.; U.S. Appl. No. 12/614,226 entitled "Systems and Methods for Treatment of BPH," filed Nov. 6, 2009.

Shadduck et al.; U.S. Appl. No. 12/687,722 entitled "Systems and Methods for Treatment of Prostatic Tissue," filed Jan. 14, 2010.

Hoey et al.; U.S. Appl. No. 12/687,734 entitled "Medical Systems and Methods," filed Jan. 14, 2010.

Hoey et al.; U.S. Appl. No. 13/072,573 entitled "Systems and Methods for Prostate Treatment," filed Mar. 25, 2011.

Hoey et al.; U.S. Appl. No. 13/352,198 entitled "Systems and methods for prostate treatment," filed Jan. 17, 2012.

Hoey et al.; U.S. Appl. No. 13/595,914 entitled "Systems and Methods for Treatment of Prostatic Tissue," filed Aug. 27, 2012.

* cited by examiner

METHODS FOR TREATMENT OF PROSTATIC TISSUE

CROSS REFERENCE TO RELATED APPLICATIONS

This application claims the benefit under 35 U.S.C. 119 of U.S. Provisional Patent Application No. 61/112,099, filed Nov. 6, 2008, titled "Systems and Methods for Treatment of Prostatic Tissue." This application is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates to an apparatus and a related method for the minimally invasive treatment of prostate tissue.

BACKGROUND OF THE INVENTION

Several systems and methods have been developed or proposed for the treatment of prostate tissue to alleviate BPH symptoms or to treat prostate tissue. For example, tissue ablation methods have been based on RF ablation, microwave ablation, high intensity focused ultrasound (HIFU), cryoablation, radiation, surgery, and brachytherapy. Surgical methods with and without robotic assistance have been developed for removal of diseased prostate tissue.

The apparatus, techniques and methods disclosed herein are adapted for the treatment of prostate tissue in general and more particularly are focused on treatment of BPH (benign prostatic hyperplasia) and prostate cancer. BPH is a common problem experienced by men over about 50 years old that relates to urinary tract obstruction. Prostatic hyperplasia or enlargement of the prostate gland leads to compression and obstruction of the urethra which results in symptoms such as the need for frequent urination, a decrease in urinary flow, nocturia and discomfort.

Ablation of prostatic tissue with electromagnetic energy is well known and has the advantage of allowing a less invasive approach. For example, high-frequency current in a electrosurgical ablation or prostatic tissue causes cell disruption and cell death. Tissue resorption by the body's wound healing response then can result in a volumetric reduction of tissue that may be causing urinary tract obstruction. One disadvantage or high-frequency current or laser ablation is potential tissue carbonization that results in an increased inflammatory response and far longer time to heal following the ablation.

SUMMARY OF THE INVENTION

A method of treating a disorder of a prostate is provided, comprising introducing an ablation probe transurethrally into the prostate, the ablation probe having a longitudinal axis, translating the ablation probe along the longitudinal axis while injecting condensable vapor through the ablation probe into the prostate, and aspirating prostate tissue proximally through the ablation probe.

In some embodiments, the method further comprises inserting an introducer into a urethra and advancing the ablation probe through the introducer. The introducing step can comprise advancing the ablation probe into an apex of a lobe of the prostate.

In one embodiment, the method further comprises removing a core of prostate tissue. The method can also comprise rotating the ablation probe. In some embodiments, the method can include injecting a high pressure liquid through the ablation probe into the prostate.

In some embodiments, injecting condensable vapor comprises delivering between 100 W and 1000 W to the prostate. In another embodiment, injecting condensable vapor comprises delivering between 100 cal/gram and 600 cal/gram to the prostate. In another embodiment, the method comprises removing between 1 gram and 100 grams of prostate tissue from the prostate.

A prostate therapy system is provided, comprising a condensable vapor source, and an ablation probe adapted to be inserted transurethrally into a prostate lobe of an adult male human subject, the ablation probe having a vapor delivery port communicating with the vapor source and adapted to deliver condensable vapor to the prostate lobe and an aspiration port adapted to aspirate prostate tissue proximally into the ablation probe.

In some embodiments, the ablation probe is further configured to rotate within the prostate. A powered rotating motor can be adapted to rotate the ablation probe between 5 rpm and 10,000 rpm.

The prostate therapy system can further comprise a source of high pressure liquid in communication with a liquid ejection port in the ablation probe.

DETAILED DESCRIPTION OF THE INVENTION

The present invention provides for a vapor energy generation system that can be configured for introduction into a patient's urethra or prostate, or can be configured to access prostatic tissue trans-rectally or endoscopically. The system is configured to deliver a heated vapor, for example water vapor, to tissue as described in the following co-pending U.S. Patent Applications: U.S. patent application Ser. No. 10/681,625, filed Oct. 7, 2003, now U.S. Pat. No. 7,674,259, titled "Medical Instruments and Techniques for Thermally-Mediated Therapies"; No. 11/158,930 filed Jun. 22, 2005, now U.S. Pat. No. 7,892,229, titled "Medical Instruments and Techniques for Treating Pulmonary Disorders"; No. 11/244,329, filed Oct. 5, 2005, now U.S. Pat. No. 8,016,823, titled "Medical Instrument and Method of Use"; and No. 11/329,381, filed Jan. 10, 2006, titled "Medical Instrument and Method of Use".

The generation and delivery of a collapsible, high energy vapor for various therapeutic procedures is further disclosed in systems with 'remote" vapor generation systems or sources in co-pending Provisional Patent Application Nos. 60/929,632, 61/066,396, 61/068,049, or with vapor generator in a handle or working end, or combination thereof, as described in Provisional Patent Application Nos. 61/068,130, 61/123,384, 61/123,412, 61/126,651, 61/126,612, 61/126,636, 61/126,620.

Figure 1:
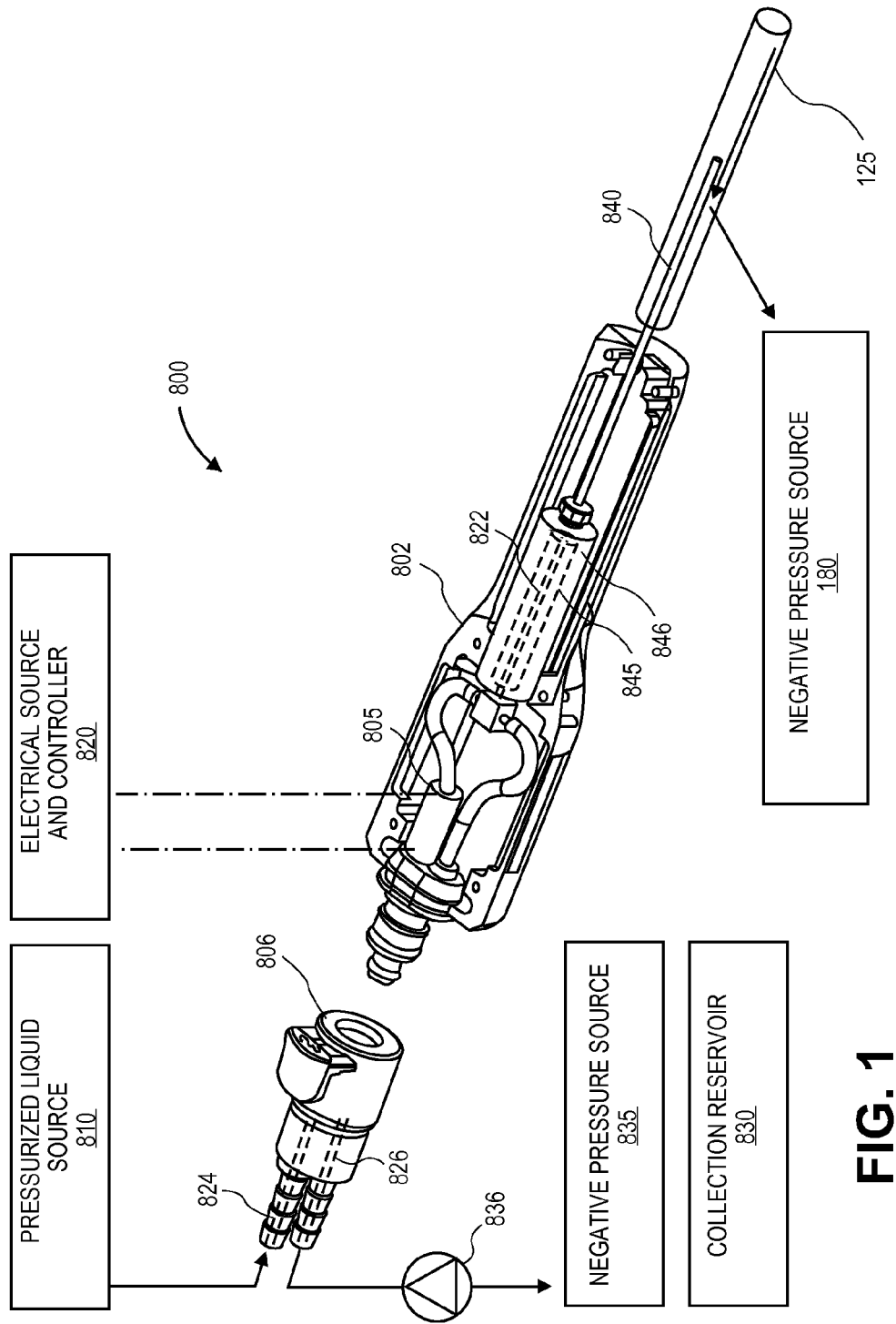
FIG. 1 is a vapor energy delivery system and more particularly a cut-away view of a handle portion of an instrument with an inductive heating assembly for applying vaporization energy to a fluid flow together with a looped flow system for maintaining a circulating flow of high energy vapor which is releasable on demand to flow through an extension member to interact with tissue.

FIG. 1 illustrates a vapor energy generation system 800 having a handle 802 comprising an inductive heating system similar to that described in applications 61/123,416, 61/123,417, 61/126,647. In FIG. 1, the handle 802 is coupled by temperature resistant fitting 806 to a pressurized liquid or fluid source 810 that delivers liquid at a controlled flow rate and pressure. The liquid flow passes through a vapor generating inductive heater 805 coupled to an electrical source and controller 820. The system and handle is configured for a looped liquid/vapor flow to provide vapor to working end or exit channel 822 to deliver the vapor to a tissue site. The system has inflow channel indicated at 824 and outflow channel at 826 that can communicate with a collection reservoir 830 and/or a negative pressure source 835. A valve 836, for example, operated by a footswitch is provided in outflow channel 826 to re-direct vapor into the exit channel 822 and extension member 840.

A vapor energy generation system 800 as shown in FIG. 1 can be used for any surgical/medical application, with the extension member 840 comprising an elongate ablation probe, a needle, a flexible catheter, or other similar elongate delivery devices. This system can be used for a catheter for delivering energy for endovascular applications, for treating respiratory tract disorders, for endometrial ablation treatments or for needle ablation treatments. In the embodiment of FIG. 1, an optional secondary heater 845 is shown with a concentric insulator 846. This secondary heater can add further vaporization energy to vapor that starts to flow through exit channel 822. The secondary heater can be an inductive heater or a resistive heater that uses a microporous material to provide a large surface area to apply energy to the vapor to remove any water droplets. This system can provide a vapor that is at least 90% water vapor. The secondary heater is operatively coupled to the electrical source and controller 820 by electrical leads (not shown).

Figure 2:
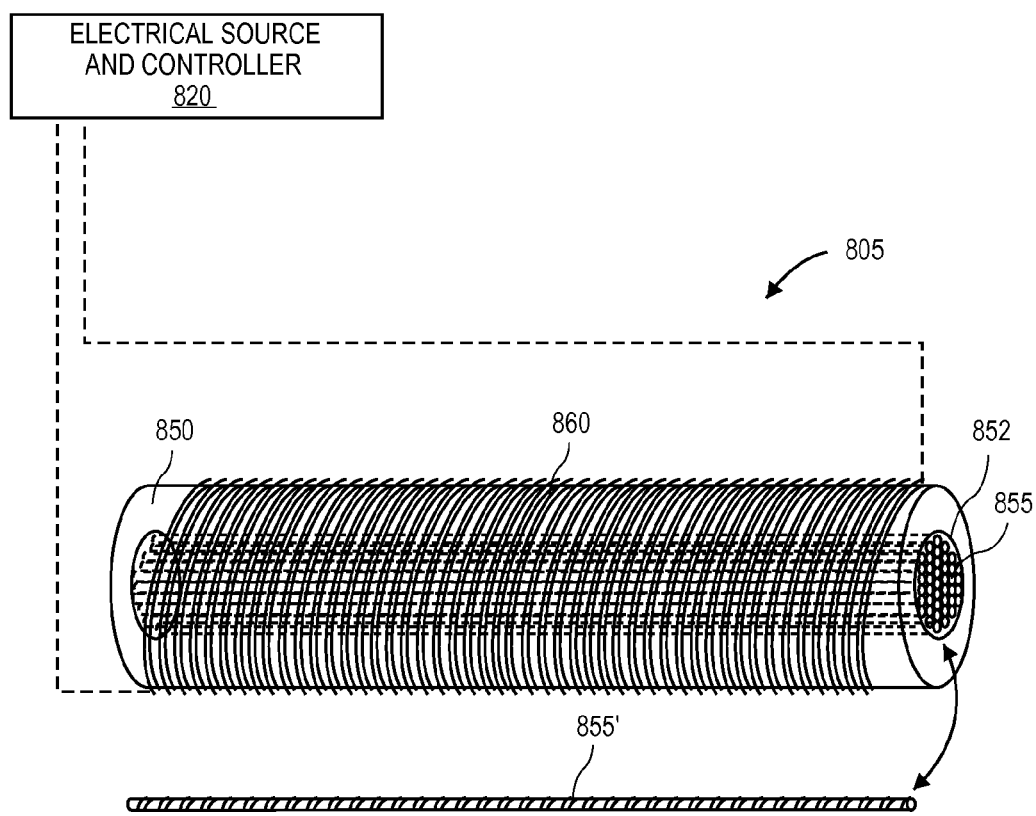
FIG. 2 is a schematic view of the inductive heating assembly of FIG. 1.

FIG. 2 illustrates a vapor generating inductive heater 805 that in one embodiment comprises a ceramic cylinder 850 with a bore 852 therein. The ceramic cylinder 850 can be approximately 1.0" to 1.5" in length and 0.25" in diameter with a 0.10" bore 852, for example. The bore 852 can be packed with a plurality of small diameter hypotubes 855 that are magnetic responsive, such as 316 stainless steel, for example. In one embodiment, the hypotubes 855 are 0.016 thin wall tubes. A winding 860 of one to ten layers having an axial length of about 1.0" can be provided about the ceramic cylinder 850 for inductive heating of the hypotubes 855 using very high frequency current from an electrical source. In one embodiment the winding 860 can be 26 Ga. Copper wire with a Teflon coating. It has been found that delivering at least 50 W, 100 W, 200 W, 300 W, 400 W, or 600 W with suitable flow rates of water can produce very high quality vapor, for example 90% vapor and better.

In FIG. 2, it can be seen that an inductively heated hypotube 855' also can be spiral cut to provide flexibility for such an inductive heater to be positioned in a catheter or probe working end. For example, such flexible heatable elements can be carried in the bore of a flexible high temperature resistant polymeric insulative member to provide a flexible catheter that is configured for endovascular navigation. An insulation layer about an exterior of the inductive heater is not shown. In general, the vapor generating inductive heater 805 can be configured to provide a high quality vapor media with precise parameters in terms of vapor quality, exit vapor pressure from a working end, exit vapor temperature, and maintenance of the parameters within a tight range over a treatment interval. All these parameters can be controlled with a high level of precision to achieve controlled dosimetry, whether the particular treatment calls for very low pressures (e.g., 1-5 psi) or very high pressures (200 psi or greater) over a treatment interval, and whether the treatment interval is in the 1-10 second range or 2 to 5 minute range.

Figure 3:
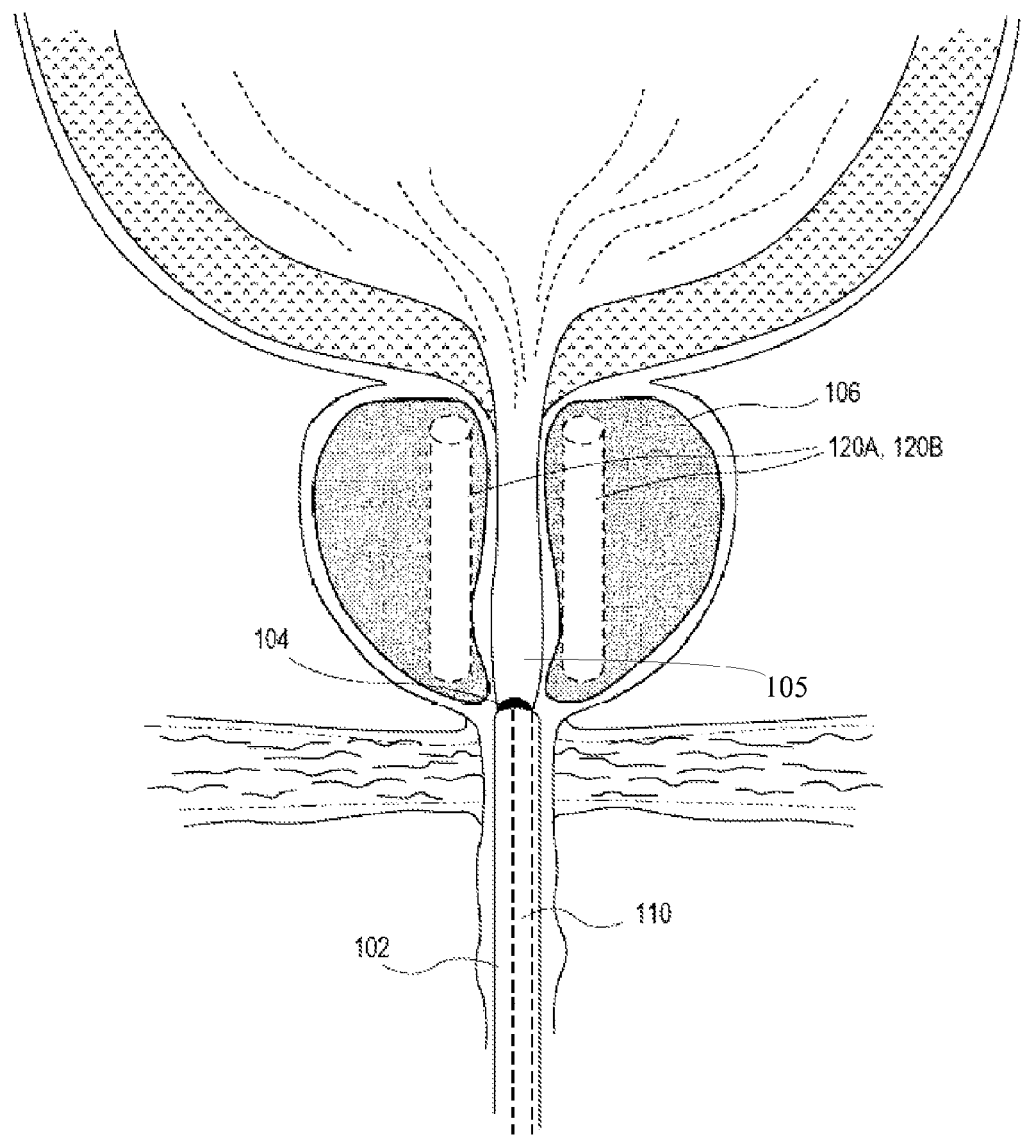
FIG. 3 is a schematic view of a patient prostate and a first step of introducing a tissue-selective extraction device into a patient urethra, showing tissue volumes targeted for 'coring' or extraction.
Figure 4:
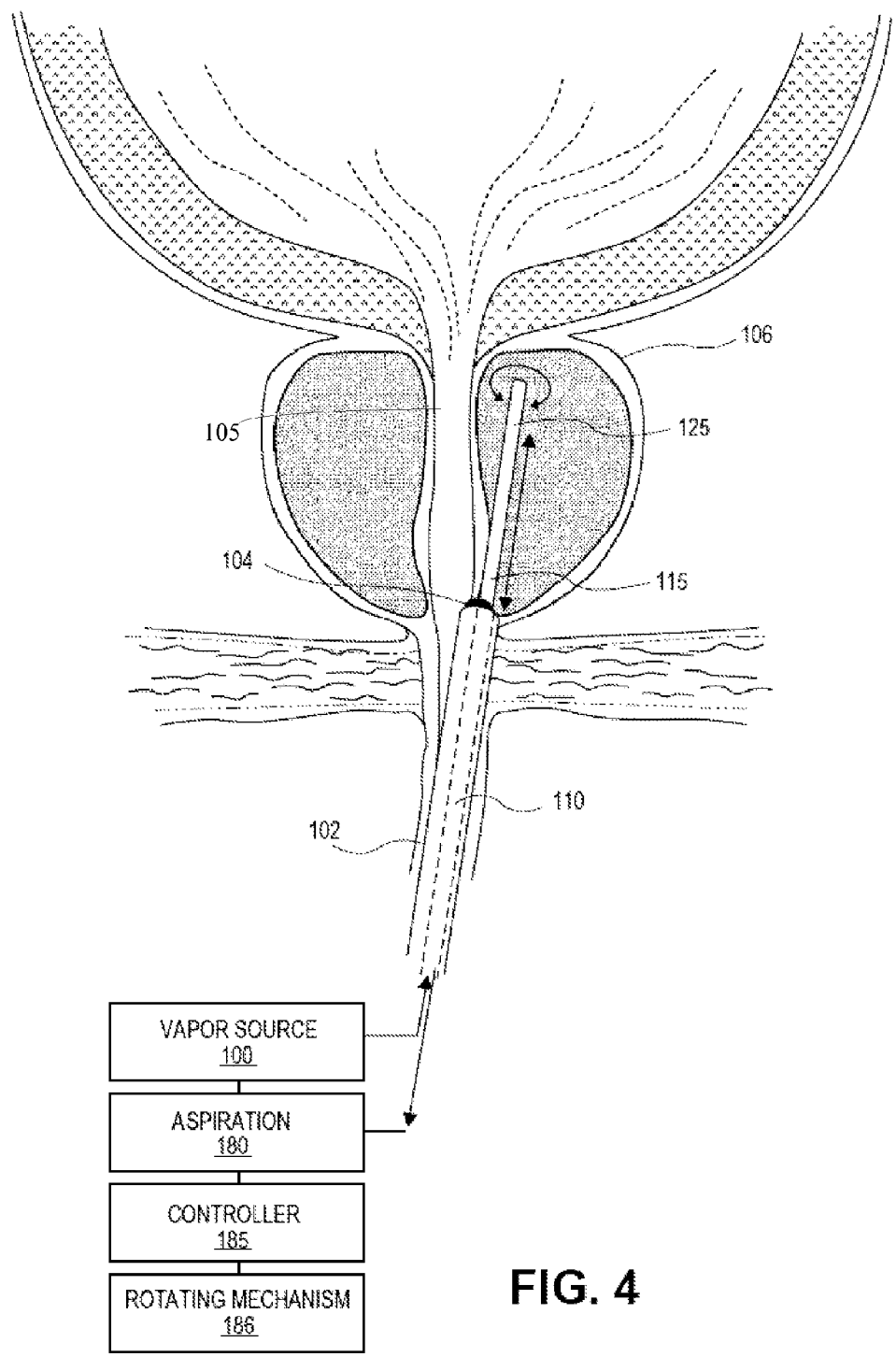
FIG. 4 is a schematic view of the patient prostate of FIG. 3 with a subsequent step of introducing the working end or the tissue-selective extraction device into a proximal aspect of the prostate and through the prostate adjacent the urethra.

Now turning to FIGS. 3-4, a system including an elongated introducer 102 with imaging system 104 is introduced into a patient urethra 105 within prostate 106 and navigated to a predetermined location wherein the distal end of the instrument and imaging system 104 can identify anatomical landmarks. In one embodiment, the introducer 102 has an axial channel 110 that carries an extendable ablation probe 115, as shown in FIG. 4. In FIG. 3, it can be seen that tissue region or cores 120A and 120B in the opposing lobes of the prostate are targeted for removal together with thermal sealing of the margins of the extracted tissue volumes. The ablation probe 115 is adapted to be inserted transurethrally into a prostate lobe of a male subject to deliver condensable vapor to the prostate lobe and aspirate prostate tissue proximally into the ablation probe.

Referring to FIG. 4, the ablation probe 115 has a working end 125 that is configured for applying mechanical and thermal energy to prostate tissue for ablation and volumetric removal of the tissue adjacent the urethra. The working end can be from about 2 to 6 mm in diameter, for example. The working end 125 can be translated axially back and forth within the prostate to ablate and remove tissue in a method depicted in FIG. 5. In addition, referring back to FIG. 4, the ablation probe is operatively coupled to vapor source 100, aspiration 180, and controller 185. The vapor source 100 can be a condensable vapor source, such as the vapor energy generation system described above in FIG. 1. Aspiration 180 can be a negative pressure or vacuum source to provide suction to the ablation probe, and controller 185 can be used to control the delivery of vapor to a patient as well as the aspiration of tissue from the patient. The controller can comprise a computer or CPU and controls (e.g., a joystick, buttons or levers on the proximal end of the ablation probe, a mouse/keyboard, etc) for use by a physician to control vapor delivery and suction during the surgical procedure.

Figure 5:
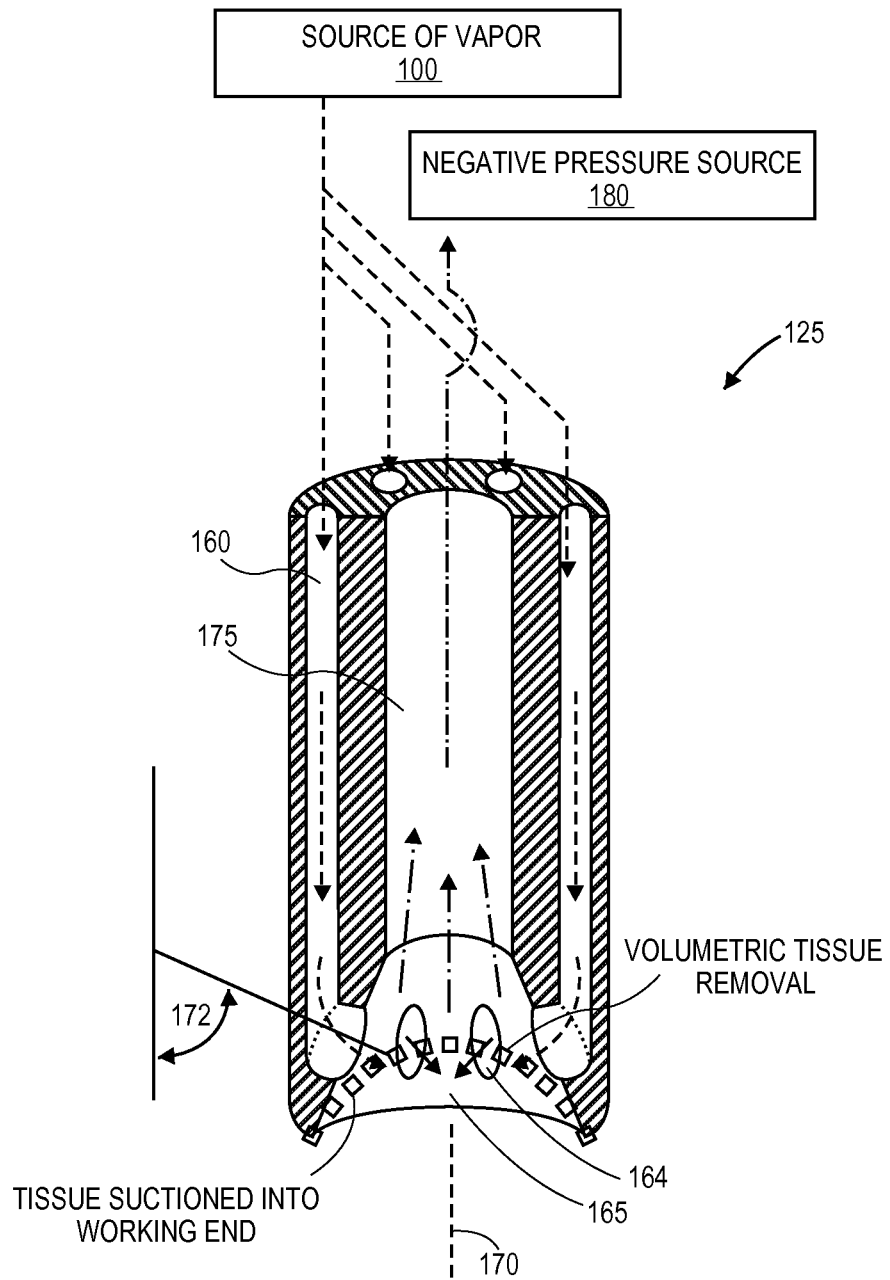
FIG. 5 is a sectional view of the working end of FIG. 4 illustrating schematically how tissue is selectively extracted.

The instrument working end 125 is shown in sectional view in FIG. 5 where it can be seen that a vapor system or source 100 (such as a source described in FIG. 1) is fluidly coupled to at least one vapor inflow channel 160 that extends to at least one vapor delivery port 164 in a recess 165 of the distal end of the device. The axis of each vapor delivery port can be directed non-axially relative to the axis 170 the instrument and the axes are directed inward toward the device axis 170. The axes of vapor ejection can have an angle 172 of between about 10° to 90° relative to axis 170.

Still referring to FIG. 5, the ablation probe 115 has an aspiration port 175 in fluid communication with an aspiration or negative pressure source 180 and a controller (not illustrated) for suctioning tissue into the working end recess 165 and extracting vapor and tissue detritus. The aspiration port is adapted to aspirate prostate tissue proximally into the ablation probe. In use, it can be understood that high pressure injection of vapor from ports 164 as depicted in FIG. 5 will cause thermal damage, weakening and denaturation of proteins and tissue constituents while at the same time the vapor and water droplets therein can apply sufficient mechanical forces to disintegrate and volumetrically remove tissue at the vapor-tissue interface. In one embodiment, the quality of the vapor, or combination of jetted vapor with jetted water droplets can cut the thermally weakened tissue.

Referring to FIGS. 3-5, it can be understood how translating the working end 125 axially while actuating the vapor flow and negative pressure source can core out volumes in prostatic tissue (FIG. 3). Additionally, referring to FIG. 4, the working end 125 can be rotated during vapor delivery and aspiration for additional coring. Rotation of the working end can be manual (e.g., physical rotation of the instrument by the physician) or, alternatively, a rotating mechanism 186 (e.g., a powered rotating motor) can be coupled to the working end 125 to automatically rotate the distal end of the device during ablation and aspiration. The rotating mechanism can be configured to rotate the ablation probe between 5 rpm and 10,000 rpm, for example. Further details of a method of rotating an ablation probe in tissue are describe in U.S. patent application Ser. Nos. 12/389,808 and 61/123,416, which are incorporated herein by reference.

The vapor flow and phase change energy release contemporaneously seals or coagulated the tissue margins to prevent bleeding. Following the treatment, the body's wound healing response return the prostate to a healed condition more rapidly than other methods that ablate a similar tissue volume in situ, since the tissue burden to be resorbed is greatly reduced. In order to advance the working end 125 through the wall of the urethra, a sharp-tipped sleeve (not shown) may be used to penetrate the wall of the lumen.

Figure 6:
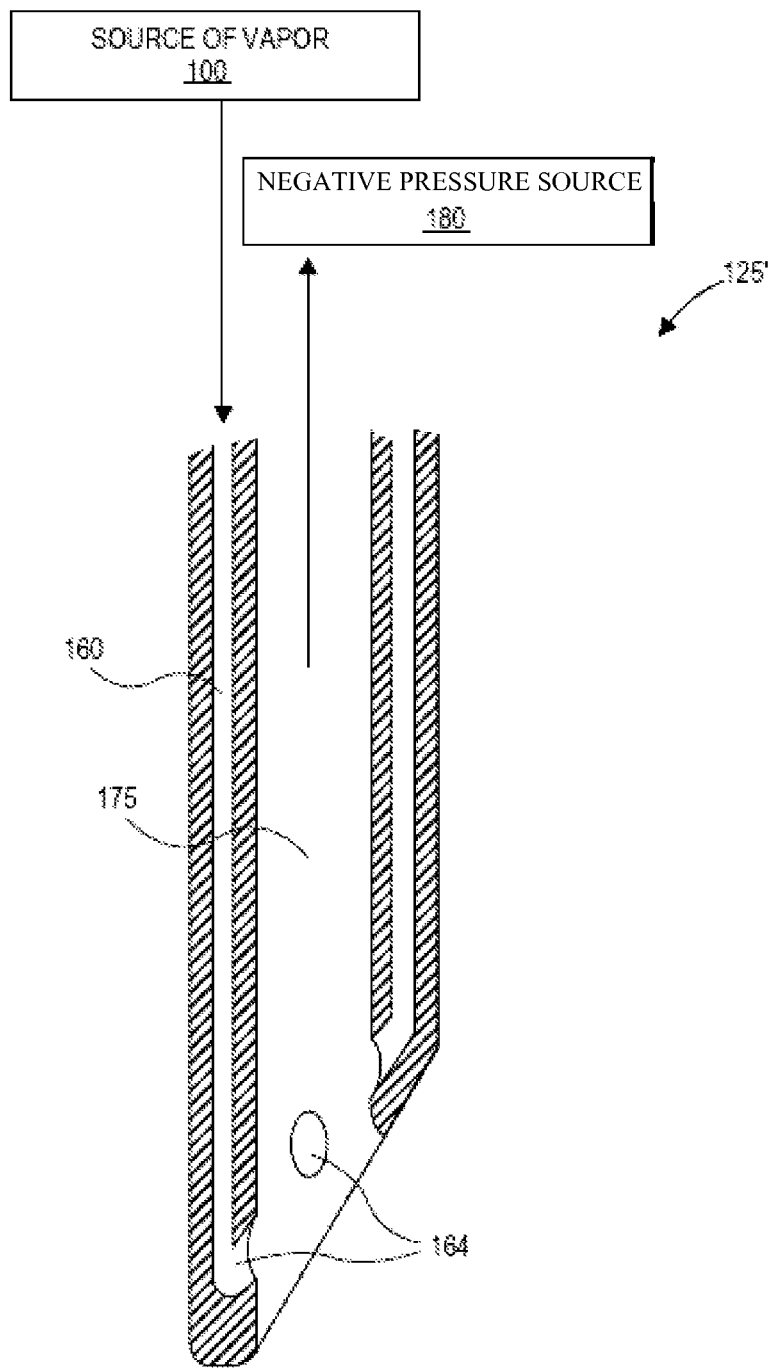
FIG. 6 is a schematic view of another instrument working end.

FIG. 6 illustrates another embodiment similar to that of FIG. 5 with working end 125' having similar functionality with the tissue receiving and ablation structure being oriented at an angle relative to the axis of the device. The angled working surface is thus adapted to ablate, disintegrate and extract tissue somewhat to the side of the device and a method of use included includes low speed or high speed rotation in conjunction with axial translation.

Figure 7:
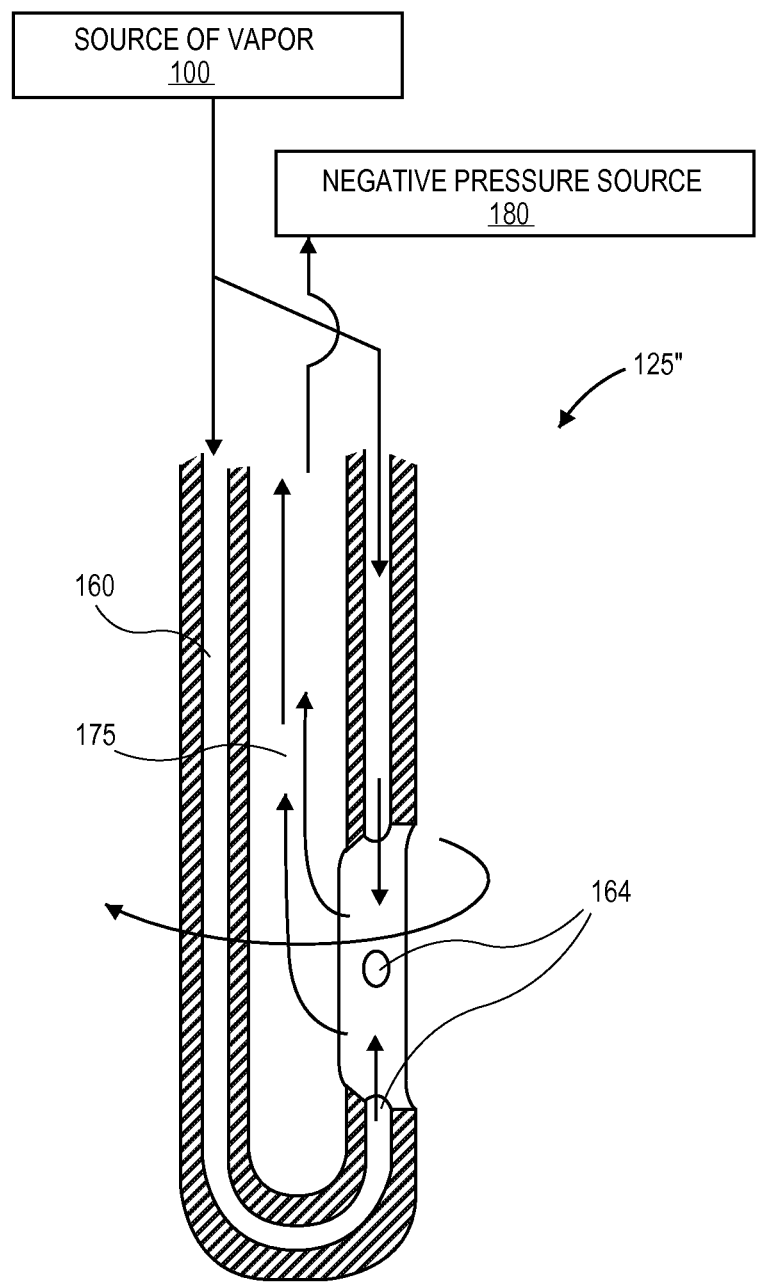
FIG. 7 is a schematic view of another instrument working end.

FIG. 7 illustrates another embodiment similar to that of FIGS. 5-6 with working end 125" having similar functionality with the tissue receiving and ablation structure being oriented at a side of the extension member substantially parallel to the axis of the device. The side extraction port is thus adapted to ablate, disintegrate and extract tissue and a method of use includes low speed or high speed rotation in conjunction with axial translation.

Figure 8:
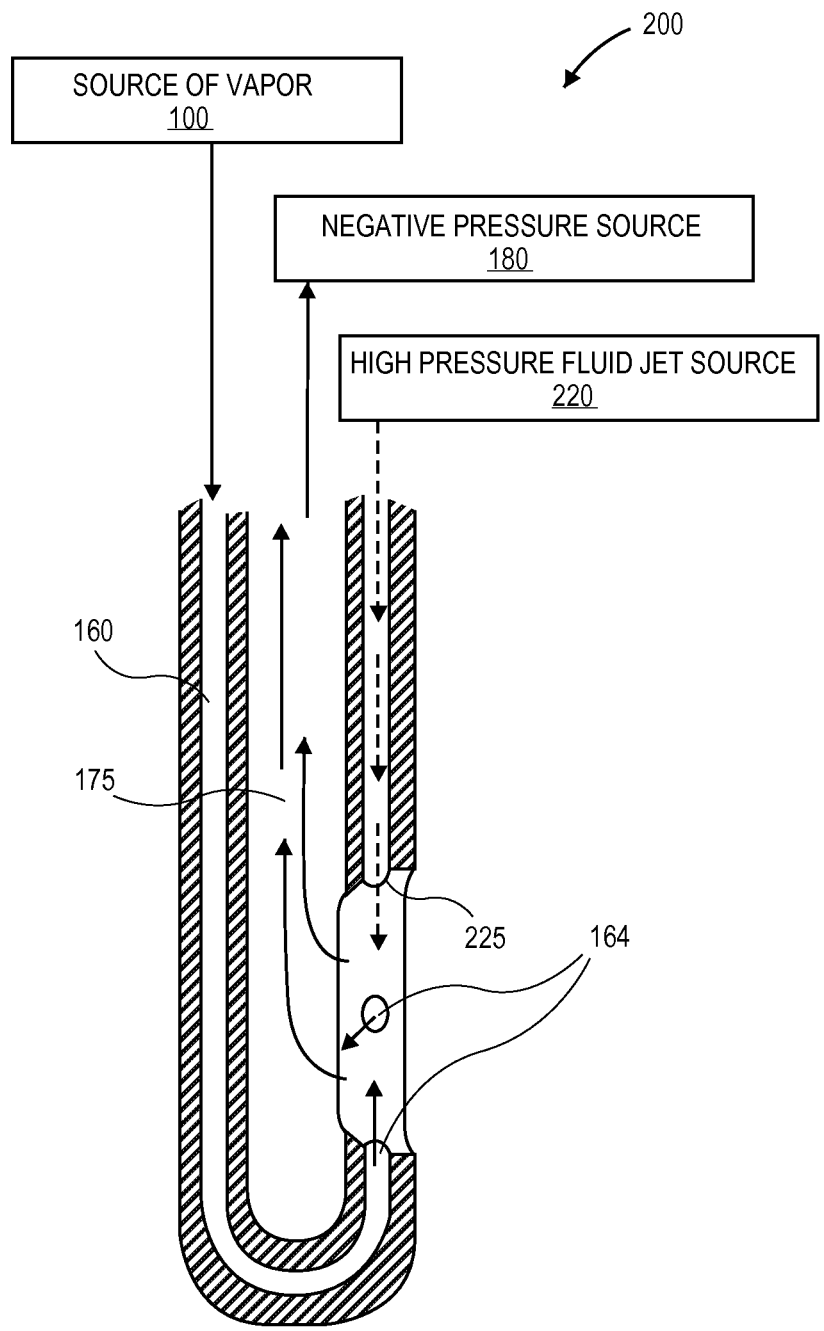
FIG. 8 is a schematic view of another instrument working end.

FIG. 8 illustrates another embodiment similar to that of FIGS. 5-7 with working end 200 that again is adapted to ablate, disintegrate and extract tissue at a side of the extension member substantially parallel to the axis of the device. In this embodiment, the system includes a very high pressure liquid fluid jetting source 220 that communicates with a liquid ejection port 225 in the working end wherein the ejected liquid is disintegrating, obliterating or cutting tissue. The system also includes a vapor source as described previously for ejecting high temperature vapor from at least one port to seal the margins of the disintegrated tissue.

Figure 9:
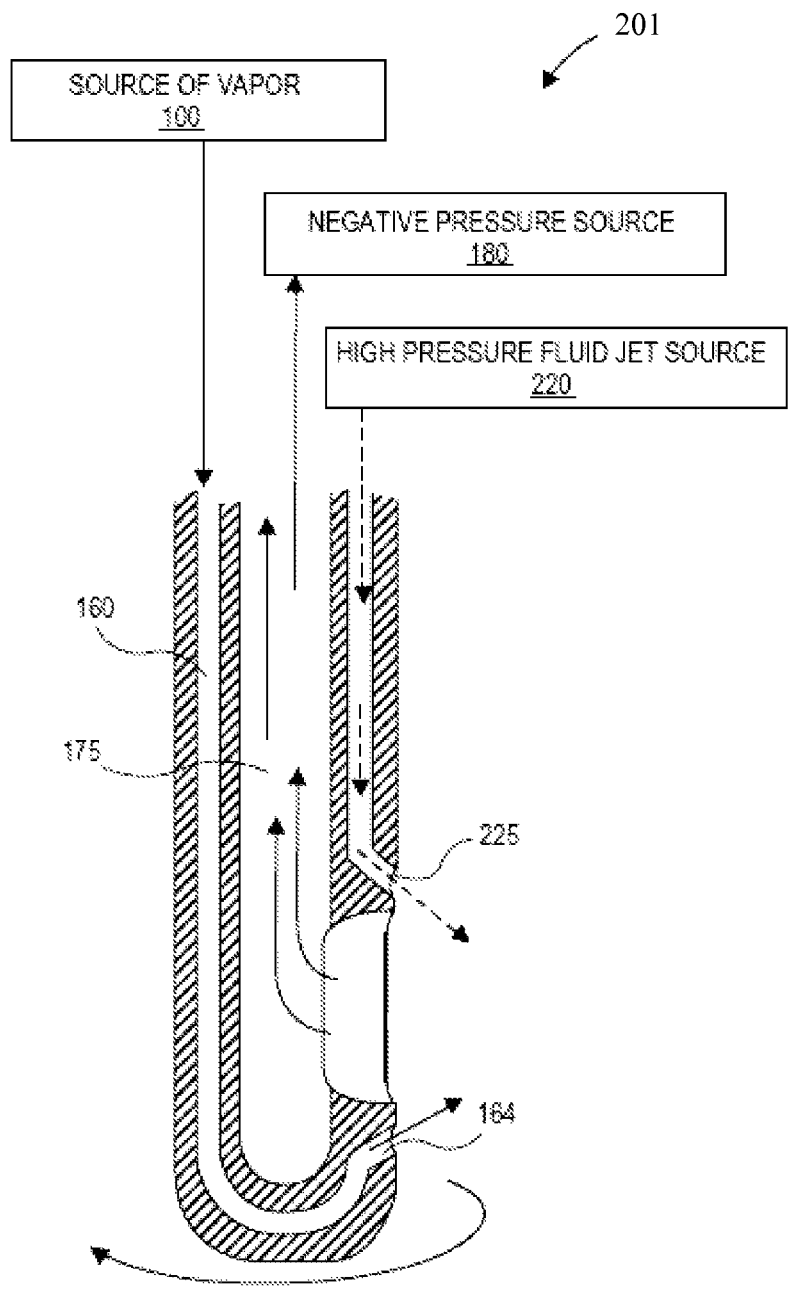
FIG. 9 is a schematic view of another instrument working end.

FIG. 9 illustrates another embodiment similar of working end 201 that is adapted to ablate, disintegrate and extract tissue at a side of the extension member similar to that of FIG. 8. The embodiment of FIG. 9 has a high pressure liquid fluid jetting source 220 with a liquid ejection port 225 that is directed outward from the axis of the device. The vapor delivery port is similarly oriented. In a method of use, the working end can be rotated at high speed, as described above in FIG. 4, to insure that the fluid jet only cuts or disintegrates tissue to a controlled, limited depth.

Figure 10:
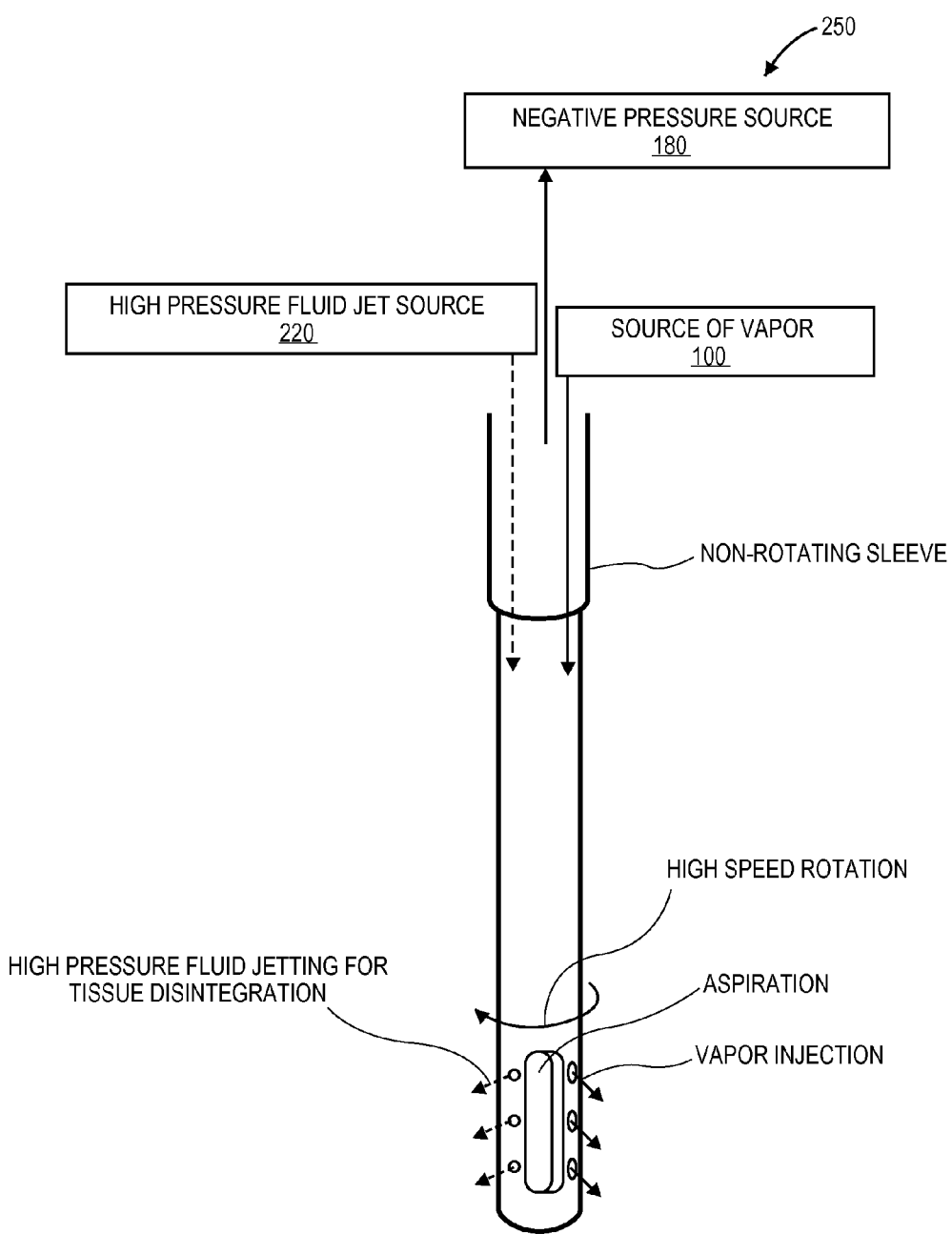
FIG. 10 is a schematic view of another instrument working end.

FIG. 10 illustrates another embodiment of working end 250 that is adapted to ablate, disintegrate and extract tissue similar to that of FIG. 8. The embodiment of FIG. 10 has a high pressure liquid fluid jetting source 220 with liquid ejection port(s) that are leading the aspiration port when rotated at high speed. The vapor delivery port(s) are exposed to lag behind the aspiration port when rotating at any high speed from about 5 rpm to 10,000 rpm. In one method, the fluid jet is pulsed at a rate of 1 to 100 pulses/second. In another embodiment, the fluid jetting is pulsed with intermittent pulses of water and vapor at a high repetition rate with the jetted water aliquot capable of disintegrating tissue and the vapor aliquot configured to weaken tissue and thermally seal tissue.

In another embodiment, the working end can carry first and second outlets for jetting with axes that at angled to intersect to cause a controlled depth disintegration of tissue.

In general, a method for treating a disorder of the prostate comprises volumetrically removing prostatic tissue in at least one lobe substantially without damage to the patient urethra. The method of volumetrically removing tissue can be performed with the ejection of a heated fluid such as a condensable vapor from a device working end and aspiration of the disintegrated tissue. In one aspect of the invention, the ejection of fluid media applies sufficient thermal energy to substantially modify tissue, wherein the modification consists of at least one of weakening covalent bonds, denaturing proteins and disrupting collagen structures. Further, the ejection of fluid media applies sufficient mechanical energy for tissue removal wherein removal consists of at least one of disintegrating, cutting, excising and ablating tissue. In another aspect of the invention, the ejection of fluid media applies sufficient thermal energy to seal or coagulate margins of the removed tissue. Also, the methods of volumetrically removing tissue can be performed contemporaneous with imaging, such as ultrasound imaging.

In general, a method for treating a prostate disorder comprises volumetrically removing prostatic tissue radially outward from the urethra in at least one lobe while maintaining urethral patency. The method volumetrically removes tissue with the ejection of a heated vapor media from a device working end and aspiration of the disintegrated tissue. The method applies energy to the prostate from the injected condensable vapor that is equal to at least 100 W, 250 W, 500 W, and 1000 W. In another embodiment, injecting condensable vapor into the prostate delivers between 100 cal/gram and 600 cal/gram to the prostate.

In general, a method for treating a prostate disorder comprises volumetrically removing prostatic tissue equaling at least 10 grams, at least 20 grams, at least 30 grams, at least 40 grams, and at least 50 grams. In another embodiment, between 1 gram and 100 grams of prostate tissue can be removed. The method includes thermally coagulating the margins about the removed tissue. A method of the invention comprises cutting and extracting at least one region of prostatic tissue while maintaining urethral patency.

In one embodiment, a method of treating a disorder of the prostate comprises introducing an ablation probe transurethrally in the prostate, translating the ablation probe along a longitudinal axis of the ablation probe while injecting condensable vapor through the ablation probe into the prostate, and aspirating tissue proximally through the ablation probe. A core of prostate tissue can be removed with this method. In some embodiments, the ablation probe can be rotated during injection of vapor and aspiration of tissue. In other embodiments, a high pressure liquid can be injected through the ablation probe into the prostate.

To gain access to the prostate, an introducer can be introduced into the urethra, and the ablation probe can be advanced through the introducer. The ablation probe can then be advanced into an apex of a lobe of the prostate.

A system comprises an elongated tissue extraction member with a working end configured for interstitial penetration in a patient prostate, a vapor source in fluid communication with vapor delivery ports in the distal end, and a negative pressure source coupled to a channel in fluid communication with a tissue extraction port in the working end proximate the vapor delivery ports. The port(s) can be oriented distally relative to an axis of the tissue extraction member, or at an angle relative to an axis of the tissue extraction member, or oriented at a side of tissue extraction member substantially parallel to the axis of the tissue extraction member.

In one embodiment, a prostate therapy system comprises a condensable vapor source, an ablation probe adapted to be inserted transurethrally into a prostate lobe of an adult male human subject, the ablation probe having a vapor delivery port communicating with the vapor source and adapted to deliver condensable vapor to the prostate lobe and an aspiration port adapted to aspirate prostate tissue proximally into the ablation probe.

Another system comprises an elongate tissue extraction member with a working end configured for interstitial penetration in a patient prostate, a vapor source in fluid communication with at least one vapor delivery ports in the distal end for applying thermal energy to tissue, and a high pressure liquid jetting source in communication with an outlet in the distal end for disintegrating tissue. The system further includes a negative pressure source coupled to a channel in fluid communication with a tissue extraction port in the working end.

In general, the methods of the invention include delivery of a condensable vapor that undergoes a phase change to provide applied energy of at least 250 cal/gm, 300 cal/gm, 350 cal/gm, 400 cal/gm and 450 cal/gm of the vapor.

In another embodiment, the treatment with vapor can be accomplished under any suitable type of imaging. In one method, the steps can be viewed by means of ultrasound or x-ray imaging. In one method, the introducer introduction and energy delivery methods of the invention can be imaged by ultrasound system utilizing a trans-rectal ultrasound system.

In another aspect of the invention, the system may contemporaneously be used to deliver fluids to targeted locations in the prostate for medical purposes, such as for general or localized drug delivery, chemotherapy, or injections of other agents that may be activated by vapor or heat.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of treating a disorder of a prostate comprising:
   introducing an ablation probe transurethrally into the prostate, the ablation probe having a longitudinal axis;
   translating the ablation probe along the longitudinal axis while injecting condensable vapor through the ablation probe into the prostate; and
   aspirating prostate tissue proximally through the ablation probe.

2. The method of claim 1 further comprising inserting an introducer into a urethra and advancing the ablation probe through the introducer.

3. The method of claim 1 wherein the introducing step comprises advancing the ablation probe into an apex of a lobe of the prostate.

4. The method of claim 1 further comprising removing a core of prostate tissue.

5. The method of claim 1 further comprising rotating the ablation probe.

6. The method of claim 1 further comprising injecting a high pressure liquid through the ablation probe into the prostate.

7. The method of claim 1 wherein injecting condensable vapor comprises delivering between 100 W and 1000 W to the prostate.

8. The method of claim 1 wherein injecting condensable vapor comprises delivering between 250 cal/gram and 450 cal/gram to the prostate.

9. The method of claim 1 further comprising removing between 10 grams and 50 grams of prostate tissue from the prostate.

10. The method of claim 1 further comprising extracting at least one region of prostate tissue while maintaining urethral patency.

11. The method of claim 1 wherein injecting condensable vapor comprises delivering between 100 cal/gram and 600 cal/gram to the prostate.

12. The method of claim 1 further comprising removing between 1 gram and 100 grams of prostate tissue from the prostate.

* * * * *